(12) United States Patent
Krishnan

(10) Patent No.: US 6,290,647 B1
(45) Date of Patent: Sep. 18, 2001

(54) CONTRAST AGENT IMAGING WITH SUBHARMONIC AND HARMONIC SIGNALS IN DIAGNOSTIC MEDICAL ULTRASOUND

(75) Inventor: Sriram Krishnan, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/347,678

(22) Filed: Jul. 2, 1999

(51) Int. Cl.[7] .................................................. A61B 8/00
(52) U.S. Cl. ............................................. 600/441; 600/443
(58) Field of Search ............................. 600/441, 443, 600/447, 449, 444, 448

(56) References Cited

U.S. PATENT DOCUMENTS

| | | | |
|---|---|---|---|
| 5,675,554 | 10/1997 | Cole et al. | 367/138 |
| 5,685,308 | 11/1997 | Wright et al. | 128/660.7 |
| 5,827,188 | 10/1998 | Wright et al. | 600/447 |
| 5,856,955 | 1/1999 | Cole et al. | 367/138 |
| 5,882,307 | 3/1999 | Wright et al. | 600/442 |
| 5,980,459 | * 11/1999 | Chiao et al. | 600/447 |
| 6,050,944 | * 4/2000 | Holley et al. | 600/441 |
| 6,050,947 | * 4/2000 | Rhyne et al. | 600/447 |
| 6,102,858 | * 8/2000 | Hatfiled et al. | 600/443 |

* cited by examiner

Primary Examiner—Marvin M. Lateef
Assistant Examiner—Maulin Patel
(74) Attorney, Agent, or Firm—Craig A. Summerfield; Brinks Hofer Gilson & Lione

(57) ABSTRACT

The invention is directed to improvement in diagnostic medical ultrasound contrast agent imaging. Subharmonic and harmonic imaging are combined by generating a subharmonic frequency intensity value, generating a harmonic frequency intensity value, and generating display indicia as a function of both the subharmonic and harmonic intensity values. A first embodiment of the invention is directed to using predominantly harmonic information in one mode and predominantly subharmonic information in a second mode. A second embodiment of the invention is directed to combining harmonic and subharmonic information in the same mode.

20 Claims, 2 Drawing Sheets

CONTRAST AGENT IMAGING WITH SUBHARMONIC AND HARMONIC SIGNALS IN DIAGNOSTIC MEDICAL ULTRASOUND

BACKGROUND OF THE INVENTION

1. Field of Invention

This invention relates generally to an improvement in diagnostic medical ultrasound imaging, and more specifically to more effective medical imaging of a human or animal due to improved utilization of an ultrasound contrast agent.

2. Description of the Prior Art

Traditionally, ultrasound contrast agents have been imaged by using fundamental imaging or second harmonic imaging. Harmonic imaging is usually preferred over fundamental imaging, because the signal from contrast agents is much larger than that from surrounding tissue. Furthermore, harmonic imaging provides excellent contrast between blood and tissue, and is able to reduce artifacts due to phase aberrations in the body. However, since harmonic imaging still receives signal from tissue, the specificity between contrast agent and tissue is still limited.

Recently, subharmonic imaging has been recognized to be a promising new technique to image contrast agents. However, the biggest advantage of subharmonic imaging is also its biggest drawback. Since tissue does not generate subharmonic signals, clinicians cannot view the underlying anatomy.

Therefore, it would be desirable to combine the advantages of subharmonic imaging with harmonic imaging to image contrast agent and visualize background tissue.

SUMMARY OF THE INVENTION

One object of the invention is to achieve the advantages of subharmonic imaging with contrast agent while still being able to visualize background tissue.

The invention is generally directed to generating a subharmonic frequency intensity value, a harmonic frequency intensity value, and display indicia as a function of both the subharmonic and harmonic intensity values.

These and other objects and advantages of the invention will become apparent to those skilled in the art from the following detailed description of the invention and the accompanying drawings.

DETAILED DESCRIPTION OF PREFERRED EMBODIMENTS OF THE INVENTION

Figure 1:
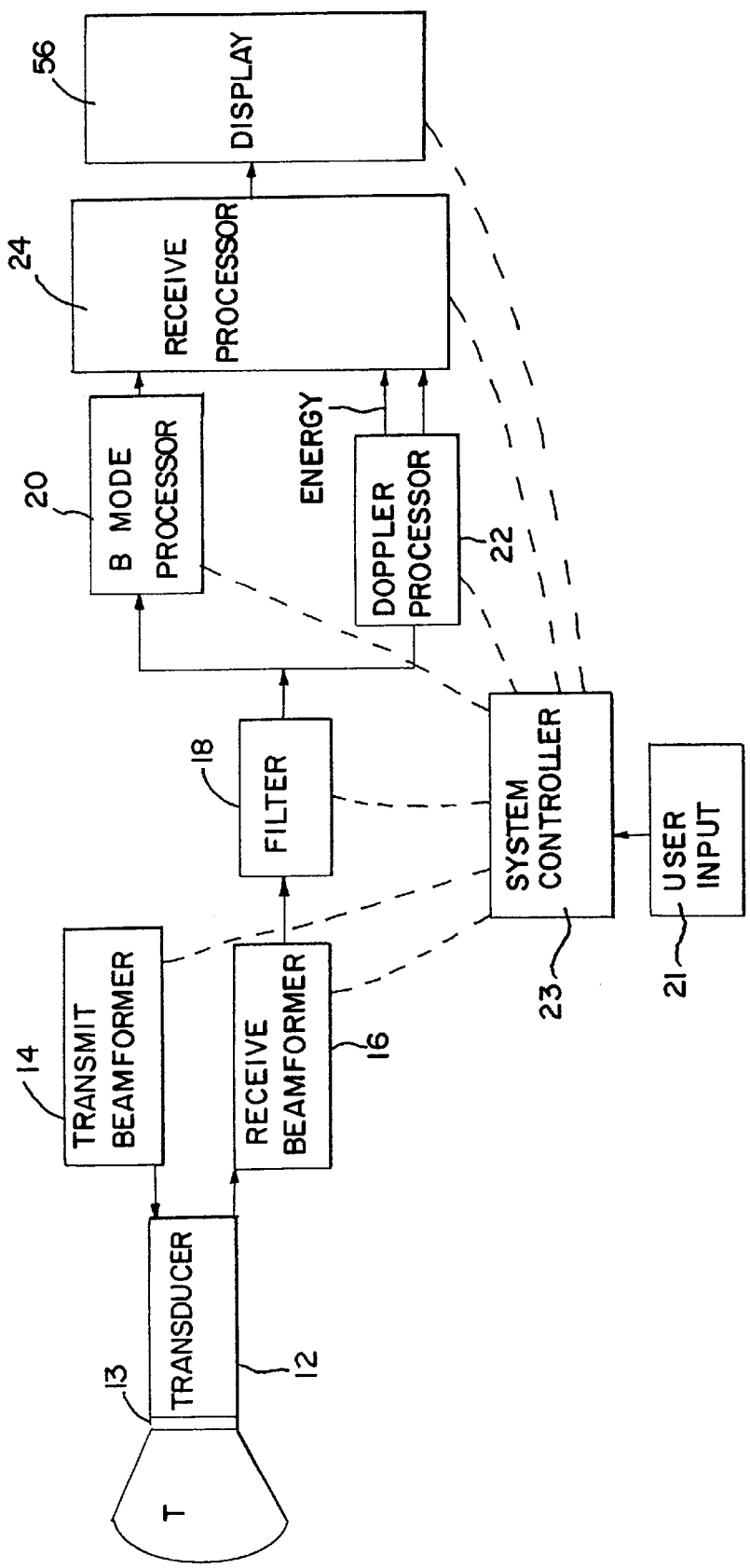
FIG. 1 is a block system diagram of a signal path carrying out a first and/or second preferred embodiment of the invention.

This invention represents an improvement to conventional subharmonic imaging of ultrasound contrast agents. It relates to combining harmonic and subharmonic image information. This combination is very useful in detecting and quantifying the presence of contrast agent.

Subharmonic imaging provides unique abilities to distinguish between contrast agents and surrounding tissue, because while contrast agents generate subharmonics at conventional diagnostic ultrasound power levels, tissue will not. Imaging using subharmonics is described in co-pending U.S. patent application Ser. No. 09/282,603, entitled "Medical Diagnostic Ultrasound Imaging System and Method with Fractional Harmonic Seed Signal," filed on Mar. 31, 1999, which is assigned to the assignee of the present invention and hereby incorporated by reference.

As used herein, "subharmonic" is intended broadly to include fractional subharmonics and ultraharmonics (e.g. 1/2, 3/2, or 5/2 of the fundamental frequency), and "harmonic" is intended broadly to include higher harmonics (e.g. 2, 3, or 4 times the fundamental frequency).

In a typical subharmonic imaging mode, the system is set up to launch a pulse that occupies a frequency band centered at the fundamental frequency $f_0$, and to receive a band of frequencies centered at $f_0/2$. Echo signals at the fundamental frequency $f_0$ are rejected, typically by use of a conventional bandpass filter centered at the subharmonic frequency. Subharmonic imaging can be done with or without a seed, as discussed in co-pending U.S. patent application Ser. No. 09/282,603. This imaging mode is quite similar to second harmonic imaging, except that instead of receiving and filtering at twice the fundamental frequency $f_0$, the ultrasound system receives and filters at half the fundamental frequency $f_0$.

However, since tissue does not generate any subharmonic signal, information from underlying tissue is lost. Therefore, it is necessary to combine subharmonic imaging with something that will provide information about underlying tissue.

Harmonic imaging has been shown to provide exquisite anatomical images. Subharmonic imaging provides excellent specificity between contrast agent and tissue. Therefore, by combining the two, the overall anatomical image quality from the harmonic imaging and the specificity from the subharmonic imaging can both be realized.

Accordingly, this invention is directed to combining subharmonic and harmonic imaging, to obtain an improved ultrasound image. There are several ways in which this combination can be achieved, with advantageous results.

In a first embodiment of the invention, B-mode and color Doppler processing are carried out using different amounts of harmonic and subharmonic information in each mode. Typically, the B-mode display would be based largely or solely on harmonic information, and the color Doppler display would be based largely or solely on subharmonic information; although there may be circumstances where the B-mode display would emphasize information from the received subharmonic signal and the color Doppler display would emphasize information form the received harmonic signal.

The combination of subharmonic and harmonic imaging in different modes could be implemented on a system similar to one that can implement the combination of fundamental and harmonic imaging in different modes. The combination of fundamental and harmonic frequency imaging in different modes (e.g., B-mode using harmonic frequency imaging and color Doppler using fundamental frequency imaging) is described in co-pending U.S. patent application Ser. No. 08/904,829, entitled "Method and Apparatus for Frequency Control of an Ultrasound System," filed on Aug. 1, 1997, which is assigned to the assignee of the present invention and hereby incorporated by reference. The combination of subharmonic imaging and harmonic imaging can also be implemented in a similar fashion to the harmonic and fundamental combination described in U.S. patent application Ser. No. 08/838,920, entitled "Ultrasound Imaging Enhancement Methods and System," filed on Apr. 11, 1997, which is assigned to the assignee of the present invention and hereby incorporated by reference in its entirety. Both of these patent applications describe combinations of fundamental imaging and harmonic imaging in different modes. By adjusting the passbands of the filters as described herein, the instant invention can be achieved.

According to a second preferred embodiment of the invention, within any given mode the displayed image is based on a combination of harmonic and subharmonic information. Accordingly, for example, in B-mode, the received harmonic echoes would contribute the background anatomical tissue information, while the received subharmonic echoes would precisely locate the contrast agent in the tissue. Similarly, a contribution could be obtained form each of the harmonic and subharmonic in color Doppler modes. Again, by adjusting the passbands of the filters, the signal processing paths of U.S. patent application Ser. No. 08/838,920 can be adapted to this invention.

In this embodiment of the invention, the ultrasound imaging system combines subharmonic and harmonic imaging frames (or lines or blocks of lines) and produces a new imaging frame (or lines or blocks of lines) which is a linear or non-linear combination of the subharmonic and harmonic imaging information. The linear combination of the subharmonic and harmonic imaging values can be as simple as addition or subtraction of the subharmonic and harmonic values, or can be a weighted sum or difference. The system can also combine the subharmonic and harmonic values in a non-linear fashion, e.g., by multiplying the subharmonic and harmonic values, or by applying a non-linear function to a sum or difference of the subharmonic and harmonic values.

In some embodiments, the subharmonic and harmonic information can be combined as a function of depth or azimuth. For example, the subharmonic signals may be weak deep in the image and/or at extreme edges of the field of view. Accordingly, it can be advantageous to emphasize the harmonic information in these locations.

The first and second preferred embodiments can be combined. For example, the image displayed from information through the B-mode processor could be based on equalized harmonic and subharmonic signal strengths, while the information from the Doppler processor could be entirely or substantially entirely based on the subharmonic information.

Figure 2:
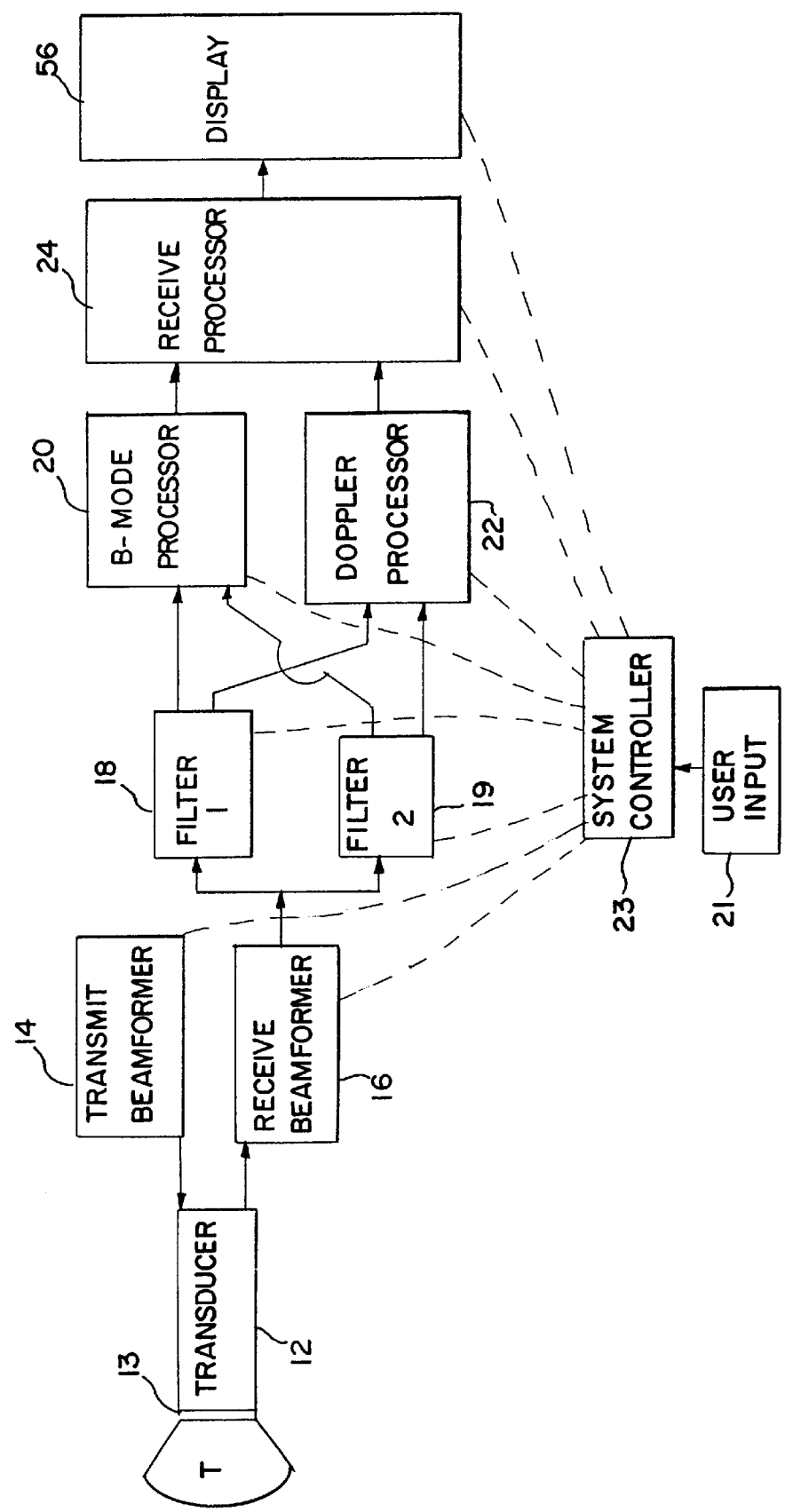
FIG. 2 is a block system diagram of an alternative signal path for carrying out a first and/or second preferred embodiment of the invention.

The preferred embodiments can be carried out, for example, as shown in FIGS. 1 or 2. In the embodiment shown in FIG. 1, two sets of firings are contemplated: for one set of firings, programmable digital filter 18 is set to pass harmonic information; for the second set of firings, the filter 18 is set to pass subharmonic information. In the embodiment shown in FIG. 2, only one set of firings is necessary, because there are two filters, filters 18 and 19, in the signal path. Of course, as known to one of ordinary skill in the art, B-mode requires as little as one firing per line, while color Doppler requires more. Accordingly, a "set of firings" means one or more firings, depending upon the modality. One of the filters can be programmed to pass subharmonic information, and the other filter can be programmed to pass harmonic information.

As discussed, the subharmonic or harmonic signals can be processed as a series of lines, blocks of lines, or frames. So, for example, the two firings in FIG. 1 could be done on a line-by-line (or block-by-block) basis, where the filter 18 is switched between harmonic and subharmonic between each successive line (or block) firing. Or, a whole frame of subharmonic data can be stored and later combined, in which case the filter 18 would only need to be switched on a frame-by-frame basis.

Referring now to FIG. 1, an ultrasound system is generally shown at 100. Ultrasound system 100 is configurable to acquire signals at a harmonic frequency band interleaved with signals at a subharmonic frequency band and display information in response to the signals, as discussed previously.

Ultrasound system 100 includes transducer 12, transmit beamformer 14, receive beamformer 16, programmable filter 18, B-mode processor 20, Doppler processor 22, system controller 23, user input 21, receive processor 24, and display 56.

The user selects the type of image or images for display with user input 21. The images are based on various processing modes known in the art. For example, a B-mode image, a M-mode image, a color M-mode image, a color Doppler velocity image (CDV), a color Doppler energy image (CDE), a Doppler Tissue image (DTI), or combinations thereof may be selected. In this specification, references to "color Doppler" are intended to generically include CDV, CDE, and DTI (including Doppler Tissue Energy, Doppler Tissue Velocity, and Doppler Tissue Acceleration), and any combination of the foregoing.

The user also selects a transmit frequency and a receive frequency associated with each image. The frequencies available for selection include at least one receive frequency that is a harmonic of the transmit frequency and at least one receive frequency that is a subharmonic of the transmit frequency.

Transducer 12 comprises a phased array of transducer elements in one of various formats, such as a linear array, curvilinear array, Vector® wide view array, annular array, radial array, etc. Transmit beamformer 14 provides transmit waveforms to transducer 12, causing transducer 12 to emit ultrasonic pulses, centered at a selected fundamental frequency, into the body tissue T, which contains both tissue and contrast agent scatterers. Appropriate transmit waveforms for subharmonic and harmonic imaging are described in a co-pending patent application, entitled "Contrast Agent Imaging with Destruction Pulses in Diagnostic Medical Ultrasound," filed on the same day as this patent application, assigned to the assignee of the present invention and hereby incorporated by reference. Ultrasound pulse scattering from the scatterers in the body returns ultrasound pulses to transducer 12, which sends signal waveforms to receive beamformer 16. Disclosures of beamformers are available: for example, receive beamformers are described in U.S. Pat. No. 5,685,308, U.S. Pat. No. 5,882,307, and U.S. Pat. No. 5,827,188 to Wright, et al.; and transmit beamformers are described in U.S. Pat. No. 5,856,955 and U.S. Pat. No. 5,675,554 to Cole, et al., but other beamformers in the art can be used.

The region from which reflected energy is received will be referred to as an imaged region, and may include blood, tissue, and a non-linear contrast agent. The receive beamformer 16 is responsive to energy at the same frequency as that applied to the transducer by the transmit beamformer (the fundamental frequency) as well as a different frequency that is harmonically related to the transmit frequency (a harmonic or subharmonic frequency).

The beamformed signals generated by receive beamformer 16 are filtered by programmable filter 18 which can be used to isolate desired signals from undesired signals. For example, programmable filter 18 may be programmed to reject signals at the fundamental frequency and to pass signals at desired harmonic and/or subharmonic frequencies. The filter 18 can be either a finite impulse response (FIR) or an infinite impulse response (IIR) filter, and is preferably a programmable digital filter (although it can, of course, be any other type of filter).

The filtered signals passed by programmable filter 18 are preferably in the in-phase and quadrature (I/Q) format, and they are applied to B-mode processor 20 and/or Doppler processor 22. B-mode processor 20 converts receive signals from programmable filter 18 into detected and log compressed image signals. Doppler processor 22 estimates the Doppler signal velocity and/or energy parameters. The information generated by B-mode processor 20 and Doppler processor 22 are provided to receive processor 24. Receive processor 24 combines subharmonic and harmonic signals and provides the image information to display 56. The information for display is scan converted and displayed, as known in the art.

Based on input from the user input 21, a system controller 23, such as one or more microprocessors with one or more programs, provides control instructions to the transmit beamformer 14, the receive beamformer 16, the programmable filter 18, B-mode processor 20, Doppler processor 22, receive processor 24, and display 56.

FIG. 2 has all the elements of FIG. 1. In addition, a second filter, filter 19, is provided. In this case, the same received data can be passed through both filters to extract harmonic and subharmonic information, with the result that the frame rate would be improved.

The images created and displayed by the ultrasound system are any type of image which shows contrast agent. Accordingly, in carrying out the invention, any type of ultrasound data can be used, alone or in combination. Specifically, any of the following ultrasound imaging modalities can be used in accordance with the embodiments taught herein, with either harmonic or subharmonic imaging, or a combination thereof: B-mode, Color Doppler Velocity, Color Doppler Energy, Color Doppler Variance, Doppler Tissue Velocity, Doppler Tissue Energy, Doppler Tissue Acceleration, pulse inversion B-mode, pulse inversion Doppler, or any combination thereof. Alternatively, B-mode images are acquired by using alternating line technology, such as alternating line phase (ALP), as described in a co-pending U.S. patent application Ser. No. 09/282,396, entitled "Diagnostic Ultrasound Imaging Method and System with Improved Frame Rate," filed Mar. 31, 1999, assigned to the assignee of the present invention and hereby incorporated by reference. All of these imaging modes can be carried out in a variety of ways. For example, in color Doppler modes and B-mode, data can be acquired and interleaved by line, block (i.e., a group of lines less than a frame), or frame.

The exemplary embodiments described herein are for purposes of illustration and are not intended to be limiting. For example, one of skill in the art will appreciate that the system block diagrams of FIGS. 1 and 2 are intended to be illustrative and not limiting. Specific details of implementation can be varied without departing from the scope of the invention. For example, the transmit and receive beamformers can be optionally integrated; and while it is preferred that they be programmable, this is not necessary in order to carry out the invention. Likewise, the image signals may be obtained at various points upstream of the scan converters. When more than two image signals are combined, some may be processed prior to scan conversion and others processed after scan conversion. Therefore, those skilled in the art will recognize that other embodiments could be practiced without departing from the scope and spirit of the claims set forth below.

What is claimed is:

1. A method for ultrasonically imaging a target comprising a non-linear contrast agent, said method comprising the following steps:

(a) generating a subharmonic frequency intensity value;

(b) generating a harmonic frequency intensity value; and (c) generating display indicia as a function of both the subharmonic and harmonic intensity values.

2. The method of claim 1, wherein the subharmonic frequency intensity value in step (a) is generated in color Doppler mode, and the harmonic frequency intensity value in step (b) is generated in B-mode.

3. The method of claim 1, wherein the display indicia include both a B-mode and a color Doppler display, and wherein the B-mode display is generated from both subharmonic and harmonic frequency intensity values and the color Doppler display is generated predominantly from subharmonic frequency intensity values.

4. The method of claim 1, wherein the subharmonic frequency intensity value in step (a) and the harmonic frequency intensity value in step (b) are generated in B-mode.

5. The method of claim 1, wherein the subharmonic frequency intensity value in step (a) and the harmonic frequency intensity value in step (b) are generated in color Doppler mode.

6. The method of claim 1, wherein the subharmonic frequency intensity value in step (a) is generated as a result of a first series of one or more transmitted pulses, and the harmonic frequency intensity value in step (b) is generated as a result of a second series of one or more transmitted pulses.

7. The method of claim 1, wherein the subharmonic frequency intensity value in step (a) and the harmonic frequency intensity value in step (b) are generated as a result of the same series of one or more transmitted pulses.

8. In an ultrasonic imaging system for simultaneously displaying both subharmonic and harmonic frequency information, said system comprising:

a programmable filter, for selectively passing subharmonic frequency intensity values and selectively passing harmonic frequency intensity values; and a display to display indicia as a function of both the subharmonic and harmonic frequency intensity values.

9. The system of claim 8, further comprising a processor for generating the subharmonic frequency intensity values in color Doppler mode, and a processor for generating the harmonic frequency intensity values in B-mode.

10. The system of claim 8, further comprising a processor for generating a B-mode display from both subharmonic and harmonic frequency intensity values and a processor for generating a color Doppler display predominantly from subharmonic frequency intensity values.

11. The system of claim 8, further comprising a processor for generating the subharmonic frequency intensity values and the harmonic frequency intensity values in B-mode.

12. The system of claim 8, further comprising a processor for generating the subharmonic frequency intensity values and the harmonic frequency intensity values in color Doppler mode.

13. The system of claim 8, further comprising a processor for generating the subharmonic frequency intensity values from a first series of one or more transmitted pulses, and a processor for generating the harmonic frequency intensity values from a second series of one or more transmitted pulses.

14. The system of claim 8, further comprising a processor for generating the subharmonic frequency intensity values and the harmonic frequency intensity values from the same series of one or more transmitted pulses.

15. In an ultrasonic imaging system for simultaneously displaying both subharmonic and hannonic frequency information, said system comprising:

a first filter, for passing subharmonic frequency intensity values;

a second filter, for passing harmonic frequency intensity values; and a display to display indicia as a function of both the subharmonic and harmonic frequency intensity values.

16. The system of claim 15, further comprising a processor for generating the subharmonic frequency intensity values in color Doppler mode, and a processor for generating the harmonic frequency intensity values in B-mode.

17. The system of claim 15, further comprising a processor for generating a B-mode display from both subharmonic and harmonic frequency intensity values and a processor for generating a color Doppler display predominantly from subharmonic frequency intensity values.

18. The system of claim 15, further comprising a processor for generating the subharmonic frequency intensity values and the harmonic frequency intensity values in B-mode.

19. The system of claim 15, further comprising a processor for generating the subharmonic frequency intensity values and the harmonic frequency intensity values in color Doppler mode.

20. The system of claim 15, further comprising a processor for generating the subharmonic frequency intensity values from a first series of one or more transmitted pulses, and a processor for generating the harmonic frequency intensity values from a second series of one or more transmitted pulses.

* * * * *

UNITED STATES PATENT AND TRADEMARK OFFICE
CERTIFICATE OF CORRECTION

PATENT NO. : 6,290,647 B1
DATED : September 18, 2001
INVENTOR(S) : Sriram Krishnan It is certified that error appears in the above-identified patent and that said Letters Patent is hereby corrected as shown below:

Column 3,
Line 14, delete "form" and substitute -- from -- in its place.

Column 7,
Line 6, delete "hannonic" and substitute -- harmonic -- in its place.

Signed and Sealed this

Twenty-seventh Day of August, 2002

Attest:

Attesting Officer

JAMES E. ROGAN
Director of the United States Patent and Trademark Office